United States Patent [19]

Cheminal et al.

[11] Patent Number: 5,705,718
[45] Date of Patent: Jan. 6, 1998

[54] PROCESS FOR THE PURIFICATION OF 1,1,1,2-TETRAFLUOROETHANE

[75] Inventors: Bernard Cheminal, Brignais; André Lantz, Vernaison, both of France

[73] Assignee: Elf Atochem S.A., France

[21] Appl. No.: 730,738

[22] Filed: Oct. 15, 1996

Related U.S. Application Data

[63] Continuation of Ser. No. 320,348, Oct. 11, 1994, abandoned.

[30] Foreign Application Priority Data

Oct. 13, 1993 [FR] France ................... 93 12190
Jun. 22, 1994 [FR] France ................... 94 07642

[51] Int. Cl.$^6$ .................. C07C 17/38; C07C 19/08
[52] U.S. Cl. .................. 570/177; 570/134; 570/161
[58] Field of Search .................. 570/134, 177, 570/161

[56] References Cited

U.S. PATENT DOCUMENTS

H1129  1/1993  Gumprecht ................... 570/168
4,158,675  6/1979  Potter ................... 260/653.7

FOREIGN PATENT DOCUMENTS 4-321632  11/1992  Japan.
5-32567   2/1993   Japan.

OTHER PUBLICATIONS

Database WPI, Derwent Pub. Ltd., JP-A-5 032 567 (Feb. 1993).
Database WPI, Derwent Pub. Ltd., JP-A-4 321 632 (Nov. 1992).

*Primary Examiner*—Kimberly J. Prior
*Attorney, Agent, or Firm*—Bell, Boyd & Lloyd

[57] ABSTRACT

To remove the unsaturated impurities (in particular 1-chloro-2,2-difluoroethylene and polyfluoropropenes) present in crude 1,1,1,2-tetrafluoroethane (F134a), a gaseous mixture of crude F134a, of hydrofluoric acid and of chlorine is treated in gaseous phase in the presence of a fluorination catalyst at a temperature of between 100° and 300° C. and at a pressure between atmospheric pressure and 2.5 MPa, the molar ratio HF/F134a being between 0.05 and 0.5 and the molar ratio Cl$_2$/F134a between 0.0001 and 0.1.

14 Claims, No Drawings

PROCESS FOR THE PURIFICATION OF 1,1,1,2-TETRAFLUOROETHANE

This is a continuation of application Ser. No. 08/320,348, filed on Oct. 11, 1994 now abandoned.

FIELD OF THE INVENTION

The present invention relates to the field of fluorinated hydrocarbons and its subject is more particularly the purification of 1,1,1,2-tetrafluoroethane.

BACKGROUND OF THE INVENTION

This compound, known in the trade as F134a, is intended especially to replace dichlorodifluoro-methane (F12) currently employed as refrigerant fluid but suspected of contributing to the weakening of the atmospheric ozone layer. To do this, F134a must satisfy quality standards in respect of the presence of a priori toxic impurities such as chlorofluorinated olefins.

Now, one of the industrial syntheses of F134a consists of a gas phase catalytic fluorination of trichloroethylene or of 1-chloro-2,2,2-trifluoroethane (F133a) which always gives, as a by-product, variable quantities of 1-chloro-2,2-difluoroethylene (F1122) which, given its boiling point ($-17.7°$ C.), is always found to be very difficult to remove completely from F134a (b.p.=$-26.5°$ C.) by simple distillation, especially under pressure.

F134a obtained by this process or by other processes generally also contains other olefinic compounds such as fluorinated butenes or propenes. $C_4$ olefins such as $CF_3CF=CF-CF_3$ (F1318), $CF_3CF=CHCF_3$ (F1327), $CF_3CH=CClCF_3$ (F1326) and $CF_3CH=CHCF_3$ (F1336) are not particularly troublesome because they can be separated from F134a by distillation. F134a obtained industrially, and in particular that obtained by gas phase fluorination of trichloroethylene or of F133a, generally also contains greater or lesser quantities of polyfluoropropenes such as $CF_3CH=CH_2$ (1243), $CF_3CF=CH_2$ (1234), $CF_3CF=CHF$ (1225) or their isomers, which are very difficult to separate from F134a by distillation because their boiling points are very close to that of 134a.

Many processes for purifying F134a, and in particular for removing F1122 from F134a have already been proposed. The following can thus be mentioned:

catalytic hydrogenation of F1122 and/or of other fluorinated olefins (WO 9008750, JP 02273634, JP 04095037);

adsorption of the impurities on active carbon (EP 389334) or on molecular sieve (U.S. Pat. No. 4,906,796, JP 03072437, EP 503796, EP 511612, EP 526002);

oxidation of F1122 with aqueous potassium permanganate (U.S. Pat. No. 4,129,603).

None of these processes is entirely satisfactory from the industrial view point. Thus, the treatment with aqueous permanganate requires the F134a to be dried after the purification, which considerably increases the cost of this treatment. Physical adsorption on carbon or molecular sieve can be envisaged industrially only as a finishing treatment because, bearing in mind the adsorptivity of the proposed materials, it appears quite uneconomical to treat products containing more than a few tens of ppm of adsorbable impurities. Furthermore, according to the documents referred to above, these adsorption techniques permit only the removal of F1122 and not of the $C_3$ or $C_4$ olefins. Catalytic hydrogenation requires special plants (compatible with hydrogen), which can be envisaged industrially only if the F134a itself has already been obtained by a hydrogenolysis process.

Other proposed processes, such as the fluorination of olefins using elemental fluorine (EP 548744), are also of no industrial interest.

More interesting is the technique described in U.S. Pat. No. 4,158,675, which relates to a process for purifying F1122 consisting in reacting the gases resulting from the main reaction:

without separation of the HCl, HF or unconverted F133a, in a second reactor maintained at a lower temperature than that of the main reaction. Starting with a gaseous mixture in which the F1122 content, in relation to the organic compounds, is 5300 vpm (volumes per million), the in-line treatment at 160° C. produces an F1122 content of 7 vpm.

In this process the impurity removed (F1122) is refluorinated to F133a, that is to say to a recyclable product. However, the major disadvantage of this process lies in the need to have to treat a large gas flow and hence to finish with a large reaction volume, and this results in high capital and maintenance costs. Furthermore, the process also concerns only the removal of F1122.

To avoid these disadvantages it has been proposed to treat, in gaseous phase in the absence of hydrochloric acid, a gaseous mixture of crude F134a and of HF in the presence of a fluorination catalyst (JP 04321632, EP 548742 and application FR 9209700). During this treatment the hydrofluoric acid adds to F1122 and some other (chloro)fluorinated olefins such as $CF_2=CFH$ (F1123), $CF_3CH=CHCF_3$ (F1336) and converts them into saturated compounds which are easier to separate and/or to recycle by distillation. This process is particularly elegant, but it has unfortunately been found that, while F1122 is particularly easy to remove by this method, other fluorinated olefins such as, for example, the fluoropropenes F1243, 1234 and 1225 are relatively very unreactive under these conditions and cannot be removed completely by this process.

It has furthermore been proposed to purify F134a by chlorination of F1122 and optionally of other olefinic impurities. This chlorination can be carried out in gaseous phase either by photochemical initiation (WO 93/12058) or by thermal initiation in the presence of a chlorination catalyst such as an active carbon or an alumina (JP 05032567). During this chlorination treatment the predominant olefin (F1122) is converted into F122:

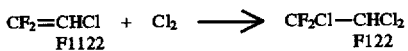

and is therefore lost. These chlorination processes are not very selective and give rise to a by-production of $CF_3CHFCl$ (F124) by chlorination of F134a, which correspondingly decreases the yield and the advantage of this purification.

To avoid the disadvantages of the abovementioned techniques, the present invention proposes a particularly effective and economical means for purifying a crude F134a containing unsaturated impurities.

DESCRIPTION OF THE INVENTION

The process according to the invention consists in treating, in gaseous phase, a gaseous mixture of crude F134a, of HF and of chlorine at a temperature of between 100° and 300° C. and at a pressure ranging from atmospheric pressure up to 2.5 MPa, in the presence of a fluorination catalyst, the molar ratio HF/F134a being between 0.05 and 0.5 and the molar ratio $Cl_2$/F134a being between 0.0001 and 0.1.

In a crude F134a the content of olefinic impurities may vary between 50 and 15,000 ppm (0.005 to 1.5%) in relation to F134a and is in most cases between 500 and 5,000 ppm (0.05 to 0.5%). Besides (chloro)fluorinated olefins, crude F134a may also contain variable quantities of other compounds such as, for example, F133a (0 to 7%), 1,1,1-trifluoroethane (F143a), monochlorotrifluoroethane (F124) and pentafluoroethane (F125); the presence of these saturated impurities does not in any way impair the effectiveness of the process according to the invention.

Among the (chloro)fluorinated olefinic impurities present in crude F134a, F1122 is generally the most important impurity. Possible other olefinic impurities such as F1123, F1243, F1234, F1225, F1318, F1327, F1326 and F1336 are either nonexistent or generally present in lower concentrations (10 to 500 ppm); among the latter the most troublesome ones are the different F1243, F1234 and F1225.

By virtue of the combined use of HF and of $Cl_2$, the process according to the invention enables most of the (chloro)fluorinated olefins to be removed practically quantitatively. It makes it possible to convert completely not only F1122, but also the $C_3$ olefins (F1243, F1234, F1225, etc.) which are particularly difficult to remove by treatment with hydrofluoric acid alone.

In the process according to the invention the (chloro) fluorinated olefins such as F1122, 1123, 1243, 1234, 1225, 1318, 1327, 1336, etc. can react either with HF or with chlorine. F1122, which is the main impurity, can thus be converted into F133a and into F122:

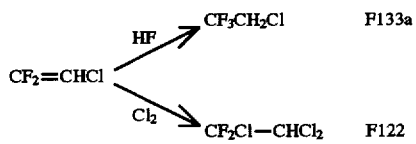

Since F133a can be recycled directly to the fluorination reactor, it is quite obviously advantageous to give priority to the former reaction. Bearing in mind the differences in reactivity with HF between F1122 and the other olefins present in crude F134a, it has been possible to demonstrate that a good choice of the operating conditions allows the by-production of F122 to be reduced to a minimum while quantitatively converting both F1122 and the other olefins such as F1243, F1234 and F1225. The fluorination of F1122 to F133a thus makes it possible to convert this impurity into a product that can be recycled to the reactor, but this preponderance of fluorination over chlorination of F1122 does not limit the invention because, in the case of low quantities of F1122, the loss by chlorination to F122 is not great.

During the use of the process according to the invention the chlorine can react with F134a or with some saturated impurities such as F133a to yield chlorination products according to the following reactions:

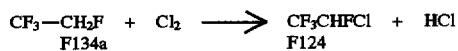
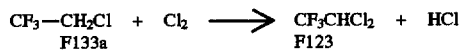

Although these chlorination products are not troublesome and can be separated from F134a by distillation, it is nevertheless advantageous to reduce these secondary reactions to a minimum because they are reflected in a loss of yield. Furthermore, these chlorination reactions release hydrochloric acid which, in the presence of the fluorination catalyst, may convert a small proportion of F134a into F133a according to the inverse reaction of that of the manufacture of F134a:

By judiciously choosing the operating conditions (temperature, contact time, $Cl_2$/F134a and HF/F134a molar ratios), it is possible to reduce these substitution reactions to a minimum and to react the chlorine practically only with the olefins. The choice of the temperature is particularly important for obtaining a selective reaction without by-production of chlorination products of F134a or possibly of F133a. However, the scope of the present invention cannot be limited to obtaining a good selectivity, because the F123 and F124 which may be by-produced are HCFCs, which are easily separable from F134a and usable as substitutes for CFCs. A loss of F134a or possibly of F133a is therefore not necessarily a considerable problem.

The gas phase catalytic treatment of crude F134a with HF and $Cl_2$ according to the invention is advantageously carried out at a temperature of between 100° and 300° C. and preferably at a pressure between atmospheric pressure and 1.5 MPa.

The contact time may vary between 10 to 200 seconds, but a contact time of between 20 and 100 seconds is preferred.

As indicated above, the molar ratio HF/F134a can vary between 0.05 and 0.5. It is preferred, however, to operate with an HF/F134a molar ratio of between 0.125 and 0.300 and, more particularly, a molar ratio close to that corresponding to the HF-134a azeotrope (0.15).

The molar ratio $Cl_2$/F134a can vary between 0.0001 and 0.1, but it is preferred to operate with a $Cl_2$/F134a molar ratio of between 0.001 and 0.03.

At the end of the treatment according to the invention the gas stream no longer contains olefinic impurities, or contains only traces thereof, and can therefore be subjected to the conventional operations (washing with water, washing with a soda-sodium sulphite solution, drying, distillation, etc.) in order to separate off the unconverted HF and chlorine and the saturated compounds other than F134a.

The fluorination catalysts to be employed for making use of the process according to the invention may be bulk catalysts or supported catalysts, the support which is stable in the reaction mixture being, for example, an active carbon, a fluorinated alumina, aluminium fluoride or aluminium phosphate.

Among the bulk catalysts, particular mention may be made of chromium oxide prepared by any one of the methods known to a person skilled in the art (sol-gel process, precipitation of the hydroxide from chromium salts, reduction of chromic anhydride, and the like). Derivatives of metals such as nickel, iron, manganese, cobalt or zinc can also be suitable by themselves or in combination with chromium, in the form of bulk catalysts, but also in the form of supported catalysts.

Supported catalysts may be employed in the form of beads, extrudates, tablets or even, when operating in a stationary bed, in the form of pieces. The tablet or bead form is generally preferred for bulk catalysts. When operating in a fluid bed it is preferable to employ a catalyst in the form of beads or extrudates.

EXAMPLES

As nonlimiting examples of catalysts there may be mentioned:

chromium oxide microbeads obtained by the sol-gel process as described in Patent FR 2 501 062, catalysts with chromium oxide deposited on active carbon (U.S. Pat. No. 4,474,895), on aluminium phosphate (Patent EP 55 958) or on aluminium fluoride (U.S. Pat. Nos. 4,579,974 and 4,579,976), mixed chromium oxide and nickel fluoride catalysts deposited on aluminium fluoride (Patent Application EP 0 486 333), bulk catalysts based on chromium and nickel oxides (Patent Application EP 0546883), nickel fluoride catalysts deposited on a fluorinated alumina.

The abovementioned patents, the content of which is incorporated here by reference, describe extensively the method of preparation of these catalysts as well as their method of activation, that is to say of preliminary conversion of the catalyst into stable active species by fluorination with gaseous HF diluted with inert compounds (nitrogen) or noninert compounds (air or 1,1,2-trichloro-1,2,2-trifluoroethane). During this activation the metal oxides used as active material (for example chromium oxide) or as support (for example alumina) may be partly or completely converted into corresponding fluorides.

The following examples illustrate the invention without limiting it. Unless shown otherwise, the contents (% and ppm) which are shown are expressed on a volume basis.

Example 1

(Comparative)

This example is intended to illustrate the reactivity of the olefins F1243, F1234 and F1225 with HF, without chlorine, in the presence of a fluorination catalyst.

100 ml of a catalyst based on nickel fluoride and chromium oxide which are deposited on aluminium fluoride were placed in a tubular reactor made of Inconel 600, 28 mm in internal diameter and 200 ml in volume. The physicochemical characteristics of this catalyst, prepared as described in Patent Application EP 0 486 333 and activated with a nitrogen/HF mixture in a stationary bed, are as follows:

Chemical composition (by weight):

Fluorine: 58.6%

Aluminium: 25.9%

Nickel: 6.4%

Chromium: 6.0%

Physical properties:

Apparent density (loose bulk): 0.85 g/ml

BET surface: 23 m$^2$/g

Volume of pores with a radius of between 4 nm and 63 μm: 0.4 ml/g

Surface of the pores with a radius greater than 4 nm: 23 m$^2$/g

After a final in-situ activation of the catalyst with the aid of an HF/F133a gaseous mixture (molar ratio: 0.4) between 25° and 250° C., the reactor was fed with a gaseous mixture consisting of HF and crude F134a in proportions such as to make the molar ratio HF/F134a equal to 0.2, that is to say close to the azeotropic composition.

The F134a employed contained 50 ppm of F1243+F1234 and 14 ppm of F1225. F1243 and F1234 were not separated under the analysis conditions (gas phase chromatography) and the 50 ppm correspond to the sum of F1243+F1234. Nevertheless, other analyses of the same mixture showed that the F1243 content was higher than that of F1234.

The absolute pressure in the reactor was set at 1.2 MPa and the feed flow rate (d) of the mixture of F134a+HF was adjusted so as to have a contact time (t) of 80 seconds, d and t being linked by the relationship:

$$t = \frac{3600 \times V \times 273 \times P \times 10}{22.4 \times d \times (T + 273)}$$

where

P=pressure in MPa t=contact time in seconds d=flow rate in moles/hour

V=volume of loosely packed catalyst expressed in liters

T=reactor temperature in degrees centigrade.

A gas sample, freed from excess HF, was analysed by VPC at the reactor exit to follow the progress of the content of olefins in the organic products.

Two tests were carried out, at 250 and 300° C. respectively (48 hours duration) and the following results were obtained:

| Content of olefins at the reactor exit (in ppm) | 250° C. | 300° C. |
| --- | --- | --- |
| F1243 + F1234 | 30 | 20 |
| F1225 | 12 | 12 |

A mixture of HF and F134a (HF/F134a molar ratio: 0.18) was then passed through the same reactor, over the same catalyst, under the same pressure and contact time conditions; the F134a contained 2400 ppm of F1122. As above, two tests were carried out, at 250° C. and 300° C., and in both cases the residual F1122 content was lower than 5 ppm.

These tests thus show very clearly that the olefins F1234, F1243 and above all F1225 are markedly less reactive towards HF than is F1122 and that it is practically impossible to remove them entirely.

Example 2

A Cl$_2$/HF/F134a mixture is passed through the same reactor and with the same catalyst as in Comparative Example 1, under the following conditions:

Pressure: 1.2 MPa

Contact time: 80 s

HF/F134a molar ratio: 0.2

Cl$_2$/F134a molar ratio: 0.001 to 0.01

Temperature: 150° to 275° C.

The F134a contained 40 ppm of F1243+F1234 and 5 ppm of F1225.

The following results were obtained:

| Temperature (°C.) | Cl$_2$/F134a molar ratio | Residual olefin contents (ppm) F1234 + F1234 | F1225 | Content of F133a and F124 formed (%) F124 | F133a |
|---|---|---|---|---|---|
| 275 | 0.01 | 4 | 3 | 0.9 | 0.9 |
| 250 | 0.01 | <1 | 2 | 0.8 | 0.8 |
| 200 | 0.01 | <1 | <1 | 0.02 | 0.005 |
| 150 | 0.01 | <1 | 3 | 0.002 | 0.0005 |
| 275 | 0.001 | 25 | 4 | 0.08 | 0.09 |

These results show that the simultaneous action of Cl$_2$ and of HF allows the olefins F1243, F1234 and F1225 to be removed completely. At temperatures above 200° C. the excess chlorine is consumed to chlorinate a little F134a to F124 with simultaneous formation of F133a. On the other hand, at 200° C. or at temperatures lower than 200° C. the reaction is much more selective and the reaction of chlorination of F134a to F124 becomes quite negligible.

Example 3

A mixture of F134a—HF—Cl$_2$ was passed through the same reactor as that employed above and containing the same catalyst, under the following conditions:
Pressure: 1.2 MPa
Contact time: 80 s
HF/F134a molar ratio: 0.2
Cl$_2$/F134a molar ratio: 0.005 to 0.02
Temperature: 150° to 275° C.

The F134a employed was an industrial product containing, among others, the following impurities:
F133a: 3.37%
F124: 1.95%
F1122: 1370 ppm
F1243+F1234: 173 ppm
F1225: 393 ppm The following results were obtained:

| Temperature (°C.) | Cl$_2$/F134a molar ratio | Content of uncoverted olefins (ppm) F1243 + F1234 | F1225 | F1122 | Content of F122 formed (ppm) |
|---|---|---|---|---|---|
| 150 | 0.01 | 8 | 12 | 8 | 185 |
| 200 | 0.02 | <1 | <1 | 8 | 1200 |
| 200 | 0.01 | <1 | <1 | 8 | 750 |
| 200 | 0.005 | 2 | <1 | 7 | 430 |
| 275 | 0.01 | 39 | 14 | 6 | 156 |

These results illustrate perfectly the excellent reactivity of the olefinic impurities with the mixture of Cl$_2$+HF. They also show that a decrease in the Cl$_2$/F134a molar ratio makes it possible to decrease the content of F122 formed, even at equal conversion of F1122. The contents of F134a and of F124 have not changed significantly during tests carried out at 200° C.

Apart from F122, the chromatographic analyses of the organic product leaving the reactor have shown the appearance of a number of new heavy products which have not been identified but which could correspond to the chlorination products of the C$_3$ olefins.

Example 4

50 ml of a catalyst consisting of bulk chromium oxide microbeads, prepared as described in Example 3 of Patent FR 2 501 062 were placed in a tubular reactor made of Inconel 600, 28 mm in internal diameter and 200 ml in volume. This catalytic reactor operating with a stationary bed was next fed with a mixture, in the gaseous state, consisting of crude F134a, HF and chlorine in proportions so as to make the HF/F134a molar ratio equal to 0.25 and so as to make the Cl$_2$/F134a molar ratio equal to 0.01.

The crude F134a contained the following impurities:
F124: 0.5%
F133a: 1.5%
F1122: 1200 ppm
F1243+F1234: 55 ppm
F1225: 24 ppm The reactor temperature was set at 225° C. and the feed flow rate of the mixture was adjusted so as to have a contact time of 50 seconds at a pressure of 1.5 MPa.

Analysis of the product leaving the reactor, after the removal of the excess chlorine and HF, yielded the following results:
F1122: 7 ppm
F1243+F1234: <2 ppm
F1225: <2 ppm The contents of F124 and F133a did not vary significantly.

Example 5

(a) Preparation and activation of a catalyst containing nickel on fluorinated alumina 500 ml of partially fluorinated alumina (containing overall 83% by mass of aluminium fluoride and 16% of alumina), obtained in a preceding stage by fluorination of Grace HSA alumina at around 300° C. using nitrogen and hydrofluoric acid, are placed in a rotary evaporator. This fluorinated support had, before impregnation, the following physicochemical characteristics:

Form: beads with a diameter of 1–2 mm
Apparent density: 0.57 g/ml
BET surface: 67 m$^2$/g
Pore volume: 0.72 ml/g (for radii of between 4 nm and 63 μm).

Moreover, an impregnation solution, containing 39 g of nickel chloride hexahydrate and 200 g of water, was prepared, which was then introduced over 45 minutes, at ambient temperature and at atmospheric pressure, onto the support with stirring. The catalyst was then dried under a stream of nitrogen in a fluidized bed at around 110° C. for 4 hours, then charged into an Inconel 600 reactor and activated with a nitrogen/HF mixture in a stationary bed according to the procedure described in Example 1 of Patent EP 0,486,333. After this treatment, the physicochemical characteristics of the catalyst are the following:

Chemical composition (by weight):
Fluorine: 60%
Aluminium: 30%
Nickel: 2.95%

Physical properties:
Apparent density (loose bulk): 0.66 g/ml
BET surface: 28.7 m$^2$/g
Volume of pores with a radius of between 4 nm and 63 μm: 0.59 ml/g
Surface of the pores with a radius greater than 4 nm: 33 m$^2$/g (b) Purification of F134a with Chlorine-free HF 300 ml of this catalyst were placed in a tubular reactor made of Inconel 600, 41 mm in internal diameter and 550 ml in volume, and the reactor was then fed with a crude HF/F134a mixture in proportions such as to make the molar ratio HF/F134a equal to 0.2, that is to say close to the azeotropic composition.

The starting F134a contained the following impurities:
Olefinic impurities:

42 ppm of unseparated F1243+F1234 ($C_3H_3F_3+C_3H_2F_4$)

157 ppm of F1122 ($CF_2CHCl$)

Main saturated impurities:

60 ppm of F114a ($CCl_2FCF_3$)

370 ppm of F124 ($CHClFCF_3$)

250 ppm of F133a ($CH_2ClCF_3$)

545 ppm of F143a ($CH_3CF_3$)

The reaction was carried out at 200° C. at atmospheric pressure, the feed flow rate of the HF/F134a mixture being adjusted so as to maintain a contact time of 80 seconds. In order to follow the progress of the content of olefins in the organic products, a gas sample, taken at the reactor exit, was analyzed by VPC, after removal of the hydracids (mainly HF) by washing and drying over calcium chloride. The following results were obtained:
Content of olefins at the reactor exit:

40 ppm of unseparated F1243+F1234

<1 ppm of F1122 (limit of detection)

These results show that the $C_3$ olefins (F1234 and F1243) are markedly less reactive towards HF than is F1122 and that it is practically impossible to remove them entirely by simple fluorination.

(c) Purification of F134a with HF-free $Cl_2$

A $Cl_2$/F134a mixture was passed through the same reactor and with the same catalyst under the following conditions:

Pressure: atmospheric

Contact time: 80 seconds $Cl_2$/F134a molar ratio: 0.007

Temperature: 200° C.

The F134a used contained the following impurities:
Olefinic impurities:

63 ppm of unseparated F1243+F1234 ($C_3H_3F_3+C_3H_2F_4$)

14 ppm of F1225 ($C_3HF_5$)

180 ppm of F1122 ($CF_2CHCl$)

Main saturated impurities:

30 ppm of F124 ($CHFClCF_3$)

39 ppm of F133a ($CH_2ClCF_3$)

The following results were obtained:
Content of olefins at the reactor exit:

F1234+F1243: <1 ppm (limit of detection)

F1225: <1 ppm (limit of detection)

F1122: <1 ppm (limit of detection)

Content of F133a, F123, F123a and F124 at the reactor exit:

F123+F123a: 0.085%

F124: 0.134%

F133a: 0.270%

These results show that removal of the $C_3$ olefins by chlorination is possible but is accompanied by a loss in yield by formation of F124 and of F133a.

(d) Purification of F134a with HF+$Cl_2$

A $Cl_2$/HF/F134a mixture was passed through the same reactor and with the same catalyst as above under the following conditions:

Pressure: atmospheric

Contact time: 80 seconds

HF/F134a molar ratio: 0.2

$Cl_2$/F134a molar ratio: 0.004 to 0.018

Temperature: 150° to 225° C.

The crude F134a used was the same as that in the preceding test (c).

The same catalyst charge was used for 130 hours to carry out the 6 tests summarized in the following table, the time for each test being between 19 and 24 hours.

The following results were obtained:

| Temperature (°C.) | Molar ratio $Cl_2$/F134a | Content of olefins at the reactor exit (ppm) | | Content of F133a, F123, F123a and F124 at the reactor exit (%) | | |
|---|---|---|---|---|---|---|
| | | F1234 + F1243 | F1225 | F123 + F123a | F124 | F133a |
| 150 | 0.018 | <1 | <1 | 0.020 | 0.006 | 0.002 |
| 150 | 0.010 | <1 | 4 | 0.016 | 0.004 | 0.007 |
| 150 | 0.004 | 2 | 7 | 0.010 | 0.003 | 0.008 |
| 200 | 0.009 | <1 | 2 | 0.013 | 0.004 | 0.014 |
| 200 | 0.005 | <1 | 4 | 0.014 | 0.003 | 0.033 |
| 225 | 0.004 | <1 | 3 | 0.025 | 0.020 | 0.082 |

After purification, no further trace of F1122 remained (limit of detection: <1 ppm).

These results show that employing a $Cl_2$/HF mixture makes it possible, on a catalyst containing nickel, to efficiently purify F134a. This treatment makes it possible to suppress the olefins F1234 and F1243 and most of F1225, while limiting degradation of F134a (formation of F123, F123a, F124 and F133a).

Example 6

By using an impregnation solution containing 117 g of nickel chloride hexahydrate and 150 g of water and by carrying out the reaction as in Example 5(a), a catalyst containing nickel on fluorinated alumina was prepared exhibiting the following physicochemical characteristics:
Chemical composition (by weight):

Fluorine: 61.5%

Aluminium: 27.5%

Nickel: 8.25%

Physical properties:

Apparent density (loose bulk): 0.71 g/ml

BET surface: 25 m²/g

Volume of pores with a radius of between 4 nm and 63 μm: 0.52 ml/g

Surface of the pores with a radius greater than 4 nm: 30.9 m²/g 300 ml of this catalyst were placed in the same reactor as in Example 5(b) and a $Cl_2$/HF/F134a mixture was passed therein under the following conditions:

Pressure: atmospheric

Contact time: 80 seconds

HF/F134a molar ratio: 0.2

$Cl_2$/F134a molar ratio: 0.005

Temperature: 200° C.

The crude F134a used was the same as that in Test 5(c).

Ater testing for 19 hours, the following results were obtained:
Content of olefins at the reactor exit:

F1234+F1243: <1 ppm

F1225: <1 ppm

F1122: <1 ppm

Content of F133a, F123, F123a and F124 at the reactor exit:

F123+F123a: 0.015%
F124: 0.011%
F133a: 0.048%

The test was prolonged and, after operating for 130 hours, the residual content of olefins and the contents of F133a, F123, F123a and F124 formed were identical.

Example 7

By carrying out the reaction as described in Patent Application EP 0,486,333 from nickel chloride, chromium oxide and partially fluorinated alumina, a catalyst was prepared which, after activation with a nitrogen/HF mixture in a stationary bed, has the following physicochemical characteristics:

Chemical composition (by weight):
 Fluorine: 56.9%
 Aluminium: 25.5%
 Nickel: 6.2%
 Chromium: 6.2%
 Chlorine: 0.7%

Physical properties:
 Apparent density (loose bulk): 0.84 g/ml
 BET surface: 59.1 m$^2$/g
 Volume of pores with a radius of between 4 nm and 63 μm: 0.37 ml/g
 Surface of the pores with a radius greater than 4 nm: 31 m$^2$/g 300 ml of this catalyst were placed in the same reactor as in Example 5(b) and a Cl$_2$/HF/F134a mixture was passed therein under the following conditions:

Pressure: atmospheric
Contact time: 80 seconds
HF/F134a molar ratio: 0.2
Cl$_2$/F134a molar ratio 0 to 0.01
Temperature 150° C. to 225° C.

The F123a used contained the following impurities:
Olefinic impurities:
 59 ppm of unseparated F1243+F1234 (C$_3$H$_3$F$_3$+C$_3$H$_2$F$_4$)
 14 ppm of F1225 (C$_3$HF$_5$)
 232 ppm of F1122 (CF$_2$CHCl)
Main saturated impurities:
 30 ppm of F124 (CHClFCF$_3$)
 39 ppm of F133a (CH$_2$ClCF$_3$)

The same catalyst charge was used to carry out all the tests summarized in the following table, the time for each test being between 19 and 24 hours.

| Temperature (°C.) | Molar ratio Cl$_2$/F134a | Content of olefins at the reactor exit (ppm) | | Content of F133a, F123, F123a and F124 at the reactor exit (%) | | |
|---|---|---|---|---|---|---|
| | | F1234 + F1243 | F1225 | F123 + F123a | F124 | F133a |
| 150 | 0.010 | <1 | 4 | 0.033 | 0.005 | 0.007 |
| 150 | 0.005 | 2 | 5 | 0.027 | 0.004 | 0.009 |
| 150 | 0 | 58 | 14 | 0 | 0.003 | 0.033 |
| 200 | 0.005 | <1 | 5 | 0.016 | 0.005 | 0.030 |
| 225 | 0.004 | <1 | 3 | 0.012 | 0.009 | 0.150 |

After purification, no further traces of F1122 remained (<1 ppm).

Although the invention has been described in conjunction with specifica embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereyb incorporated by reference.

We claim:

1. Process for the purification of a crude 1,1,1,2-tetrafluoroethane (F134a) containing unsaturated impurities, comprising treating a gaseous mixture of crude 1,1,1,2-tetrafluoroethane, of hydroluoric acid and of chlorine in gaseous phase at a temperature of between 150° and 275° C. and at a pressure ranging from atmospheric pressure up to 2.5 MPa, in the presence of a fluorination catalyst, the molar ratio HF/F134a being between 0.05 and 0.5 and the molar ratio Cl$_2$/F134a being between 0.0001 and 0.1.

2. Process according to claim 1, wherein the unsaturated impurities are 1-chloro-2,2-difluoroethylene and/or (chloro) fluorinated C$_3$ or C$_4$ olefins.

3. Process according to claim 1, wherein the operation is carried out at a pressure between atmospheric pressure and 1.5 MPa.

4. Process according to claim 1, wherein the contact time is between 10 and 200 seconds.

5. Process according to claim 4, wherein the contact time is between 20 and 100 seconds.

6. Process according to claim 1, wherein the molar ratio HF/F134a is between 0.125 and 0.300.

7. Process according to claim 1, wherein the molar ratio Cl$_2$/F134a is between 0.001 and 0.03.

8. Process according to claim 1, wherein the fluorination catalyst is a bulk or supported catalyst further based on chromium, iron, manganese, cobalt and/or zinc.

9. Process according to claim 8, wherein a bulk chromium oxide is used as catalyst.

10. Process according to claim 1, wherein a nickel fluoride supported on fluorinated alumina is used as catalyst.

11. Process according to claim 1, wherein a catalyst based on nickel fluoride and on chromium oxide supported on aluminium fluoride is used.

12. Process according to claim 1, wherein the temperature is between 150° and 225° C.

13. Process for the purification of a crude 1,1,1,2-tetrafluoroethane (F134a) containing unsaturated impurities, comprising treating a gaseous mixture of crude 1,1,1,2-tetrafluoroethane, of hydrofluoric acid and of chlorine in gaseous phase at a temperature of between 100° and 300° C. and at a pressure ranging from atmospheric pressure up to 2.5 MPa, in the presence of a fluorination catalyst based on nickel, the molar ratio HF/F134a being between 0.05 and 0.5 and the molar ratio Cl$_2$/F134a being between 0.0001 and 0.1.

14. Process for the purification of a crude 1,1,1,2-tetrafluoroethane (F134a) containing unsaturated impurities, comprising treating a gaseous mixture of crude 1,1,1,2-tetrafluoroethane, of hydrofluoric acid and of chlorine in gaseous phase at a temperature of between 100° and 300° C. and at a pressure ranging from atmospheric pressure up to 2.5 MPa, in the presence of a fluorination catalyst based on iron, manganese, cobalt and/or zinc, the molar ratio HF/F134a being between 0.05 and 0.5 and the molar ratio Cl$_2$/F134a being between 0.0001 and 0.1.

* * * * *